United States Patent
Richter et al.

(10) Patent No.: US 7,709,680 B2
(45) Date of Patent: May 4, 2010

(54) PREPARATION OF POLYISOCYANATES CONTAINING URETDIONE GROUPS USING PHOSPHINE CATALYSTS

(75) Inventors: Frank Richter, Leverkusen (DE); Reinhard Halpaap, Odenthal (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/082,803

(22) Filed: Apr. 14, 2008

(65) Prior Publication Data

US 2008/0262262 A1 Oct. 23, 2008

(30) Foreign Application Priority Data

Apr. 17, 2007 (DE) .................. 10 2007 018 015

(51) Int. Cl.
*C07C 249/00* (2006.01)
*C08G 18/10* (2006.01)

(52) U.S. Cl. ........................... 560/355; 528/59

(58) Field of Classification Search ............... 560/355; 528/59

See application file for complete search history.

(56) References Cited

U.S. PATENT DOCUMENTS

| | | | |
|---|---|---|---|
| 2,671,082 A | 3/1954 | Stallmann | |
| 4,476,054 A | 10/1984 | Disteldorf et al. | 260/239 |
| 4,912,210 A | 3/1990 | Disteldorf et al. | 540/202 |
| 4,929,724 A | 5/1990 | Engbert et al. | 540/202 |
| 7,067,654 B2 | 6/2006 | Richter et al. | 540/202 |
| 7,151,151 B2 | 12/2006 | Richter et al. | 528/45 |
| 2002/0028930 A1 | 3/2002 | Laas et al. | |
| 2004/0106789 A1 | 6/2004 | Richter et al. | 540/202 |
| 2005/0113551 A1 | 5/2005 | Richter et al. | 528/45 |

FOREIGN PATENT DOCUMENTS

DE 1153815 5/1969

*Primary Examiner*—Jafar Parsa
(74) *Attorney, Agent, or Firm*—Robert S. Klemz; Noland J. Cheung

(57) ABSTRACT

The invention provides a process for isocyanate dimerization (uretdione formation) and a process for preparing polyisocyanates having a high content of uretdione groups, using specific phosphines as catalysts. The phosphines have one or two tertiary alkyl radicals bound directly to phosphorus.

5 Claims, No Drawings

PREPARATION OF POLYISOCYANATES CONTAINING URETDIONE GROUPS USING PHOSPHINE CATALYSTS

CROSS-REFERENCE RELATED APPLICATION

This application claims priority under 35 U.S.C.§119(a-d) to German application Ser. No. 10 2007 018615.4, filed Apr. 17, 2007.

FIELD OF THE INVENTION

The invention relates to the use of specific phosphines as catalysts for isocyanate dimerization (uretdione formation) and a process for preparing polyisocyanates having a high content of uretdione groups.

BACKGROUND OF THE INVENTION

Aliphatic isocyanates which have uretdione groups and are based on optionally branched, linear-aliphatic diisocyanates have a particularly low viscosity. Products based on cycloaliphatic diisocyanates generally range from highly viscous to solid substances which can be used as emission-free, internally blocked crosslinkers in coating systems.

An overview of isocyanate oligomerization is given in J. Prakt. Chem./Chem. Ztg. 1994, 336, 185-200.

Tris(dialkylamino)phosphines (DE-A 3 030 513), if appropriate in combination with cocatalysts (DE-A 3 437 635), display a good selectivity for the formation of uretdione groups (uretdione selectivity). However, the serious problem of the high cancer-causing potential of their phosphorus oxides, e.g. hexamethylphosphoramide, stands in the way of their industrial use.

DE-A 3 739 549 discloses catalytic NCO dimerization using 4-dialkylaminopyridines, e.g. 4-dimethylaminopyridine (DMAP), but uretdione formation proceeds selectively only in the case of specific cycloaliphatic isocyanates such as isophorone diisocyanate (IPDI). Linear-aliphatic isocyanates such as hexamethylene diisocyanate (HDI) and branched, linear-aliphatic isocyanates such as trimethylhexane diisocyanate (TMDI) and methylpentane diisocyanate (MPDI) give mainly strongly coloured, heterogeneous reaction products when DMAP and related compounds are used.

DE-A 1 670 720 discloses the preparation of aliphatic polyisocyanates having uretdione groups, with tertiary phosphines having at least one aliphatic substituent and also boron trifluoride and its adducts being used as catalysts. It is indicated that high proportions of uretdione groups in the product can be obtained only at low conversions and reaction temperatures in the range from 50 to 80° C., with isocyanate trimers (isocyanurates and iminooxadiazinediones) and, especially at elevated temperature, other by-products such as carbodiimides or uretonimines being simultaneously formed. Uretonimines are a particular problem since they tend to liberate monomeric isocyanate during storage.

DE-A 10254878 describes the use of phosphines having at least one cycloaliphatic, P-bonded radical as catalysts for NCO dimerization. These catalysts display a significantly higher uretdione selectivity than other trialkylphosphines of the prior art. The use of a special case of these phosphines, namely representatives having bicyclic radicals, for the same use is described in DE 10354544.

SUMMARY OF THE INVENTION

It has now surprisingly been found that phosphines which have at least one tertiary alkyl radical bound directly to phosphorus are likewise well suited as catalysts for selective uretdione formation (isocyanate dimerization).

The invention provides for the use of phosphines which have one or two tertiary alkyl radicals bound directly to phosphorus in uretdione formation (isocyanate dimerization).

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

"Tertiary alkyl radicals bound directly to phosphorus" means that the carbon atom bound directly to the phosphorus is a tertiary carbon atom, i.e. a carbon atom which in addition to the C—P bond has single bonds to three further carbon atoms.

Preferred phosphines for isocyanate dimerization correspond to the formula I:

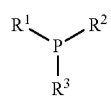

formula I where
R$^1$ is an optionally singly or multiply C$_1$-C$_{12}$-alkyl- or C$_1$-C$_{12}$-alkoxy-substituted, tertiary alkyl radical whose tertiary carbon atom is bound to the phosphorus atom via a covalent (single) bond, R$^2$ is a radical from the group consisting of primary and secondary, singly or multiply C$_1$-C$_{12}$-alkyl- or C$_1$-C$_{12}$-alkoxy-substituted, optionally branched, optionally cycloaliphatic C$_1$-C$_{20}$ radicals, with the proviso that the carbon atom bound to the P atom bears at least one hydrogen atom, and R$^3$ corresponds to R$^1$ or R$^2$.

Preferred compounds of the formula I are those in which R$^1$ is tert-butyl (2-methylprop-2-yl), tert-amyl (2-methylbut-2-yl) or adamantyl (tricyclo[3.3.1.1]dec-1-yl).

Examples of phosphines to be used according to the invention are: tert-butyldimethylphosphine, tert-butyldiethylphosphine, tert-butyldi-n-propylphosphine, tert-butyldiisopropylphosphine, tert-butyldibutylphosphine, where "butyl" can represent the isomers n-butyl, isobutyl, 2-butyl and cyclobutyl but not tert-butyl, tert-butyldihexylphosphine (all isomeric hexyl radicals which do not have tertiary carbon atoms bound directly to P), tert-butyldioctylphosphine (all isomeric octyl radicals which do not have tertiary carbon atoms bound directly to P), di-tert-butylmethylphosphine, di-tert-butylethylphosphine, di-tert-butyl-n-propylphosphine, di-tert-butyl-isopropylphosphine, di-tert-butyl-butylphosphine (all isomeric butyl radicals which do not have tertiary carbon atoms bound directly to P, see above), di-tert-butylhexylphosphine (all isomeric hexyl radicals which do not have tertiary carbon atoms bound directly to P), di-tert-butyloctylphosphine (all isomeric octyl radicals which do not have tertiary carbon atoms bound directly to P), tert-amyldimethylphosphine, tert-amyl-diethylphosphine, tert-amyldi-n-propylphosphine, tert-amyldiisopropylphosphine, tert-amyl-dibutylphosphine (all isomeric butyl radicals which do not have tertiary carbon atoms bound directly to P), tert-amyldihexylphosphine (all isomeric hexyl radicals which do not have tertiary carbon atoms bound directly to P), tert-amyldioctylphosphine (all isomeric octyl radicals which do not have tertiary carbon atoms bound directly to P), di-tert-amylmethylphosphine, di-tert-amyl-ethylphosphine, di-tert-amyl-n-propylphosphine, di-tert-amylisopropylphosphine, di-tert-amyl-butylphosphine (all isomeric butyl radicals which do not have tertiary carbon atoms bound directly to P), di-tert-amylhexylphosphine (all isomeric hexyl radicals which do not have tertiary carbon atoms bound directly to P), di-tert-amyloctylphosphine (all isomeric octyl radicals which do not have tertiary carbon atoms bound directly to P), adamantyldimethylphosphine, adamantyldiethylphosphine, adamantyldi-n-propylphosphine, adamantyldiisopropylphosphine, adamantyldibutylphosphine (all isomeric butyl radicals which do not have tertiary carbon atoms bound directly to P, see above), adamantyldihexylphosphine (all isomeric hexyl radicals which do not have tertiary carbon atoms bound directly to P), adamantyldioctylphosphine (all isomeric octyl radicals which do not have tertiary carbon atoms bound directly to P), diadamantylmethylphosphine, diadamantylethylphosphine, diadamantyl-n-propylphosphine, diadamantylisopropylphosphine, diadamantylbutylphosphine (all isomeric butyl radicals which do not have tertiary carbon atoms bound directly to P), diadamantylhexylphosphine (all isomeric hexyl radicals which do not have tertiary carbon atoms bound directly to P) and diadamantyloctylphosphine (all isomeric octyl radicals which do not have tertiary carbon atoms bound directly to P).

These can be used individually, in any mixtures with one another or in mixtures with other primary, secondary and/or tertiary alkylphosphines, aralkylphosphines and/or arylphosphines for uretdione formation.

The invention further provides a process for the dimerization of isocyanates, in which
a) at least one organic isocyanate,
b) a catalyst containing at least one phosphine which has one or two tertiary alkyl radicals bound directly to phosphorus,
c) optionally solvents and
d) optionally additives are reacted.

The amount of the catalyst to be used in the process of the invention depends first and foremost on the isocyanate used and the desired reaction rate and is in the range from 0.01 to 10 mol %, based on the sum of the molar amounts of the isocyanate used and the catalyst. Preference is given to using from 0.05 to 5 mol % of catalyst.

The catalyst b) can be used in undiluted form or as a solution in solvents in the process of the invention. Possible solvents are all compounds which do not react with phosphines, e.g. aliphatic or aromatic hydrocarbons, alcohols, ketones, esters or ethers. The phosphines are preferably used in undiluted form in the process of the invention.

As isocyanates to be used according to the invention in a), it is in principle possible to use all known organic isocyanates prepared by phosgenation or by phosgene-free processes, either individually or in any mixtures with one another.

Preference is given to using aliphatic, cycloaliphatic or araliphatic diisocyanates or polyisocyanates having an NCO functionality of $\geq 2$.

Particular preference is given to using aliphatic diisocyanates which contain optionally branched, optionally cyclic radicals and have isocyanate groups bound to a primary carbon atom. Examples are butane diisocyanate, pentane diisocyanate, hexane diisocyanate, heptane diisocyanate, octane diisocyanate, nonane diisocyanate, decane diisocyanate, undecane diisocyanate and dodecane diisocyanate, with it being possible to use any isomers of the abovementioned compounds.

Very particular preference is given to using hexamethylene diisocyanate (HDI), methylpentane diisocyanate (MPDI), trimethylhexane diisocyanate (TMDI), bis(isocyanatomethyl)cyclohexane ($H_6XDI$) and norbornane diisocyanate (NBDI), either individually or in any mixtures with one another.

It is also possible to use isophorone diisocyanate (IPDI), bis(isocyanatocyclohexyl)-methane ($H_{12}MDI$), bis(isocyanatomethyl)benzene (xylylene diisocyanate, XDI) and bis(2-isocyanatoprop-2-yl)benzene (tetramethylxylylene diisocyanate, TMXDI) in the process of the invention.

The process of the invention is carried out so that the conversion of the NCO groups is preferably from 5 to 90 mol %, in particular from 10 to 60 mol %, very particularly preferably from 10 to 50 mol %.

The process of the invention is usually carried out in the temperature range from 0° C. to 150° C.

To achieve conversions of the NCO groups within the above ranges, the reaction is stopped at the desired degree of conversion.

To stop the reaction after the desired degree of conversion has been reached, it is in principle possible to use all previously described catalyst poisons (DE-A 1670667, 1670720, 1934763, 1954093, 3437635, U.S. Pat. No. 4,614,785) such as alkylating agents (e.g. dimethyl sulphate, methyl toluenesulphonate), organic or inorganic peroxides, acid chlorides and also sulphur which are reacted with the catalyst, if appropriate with an increasing temperature (variant A, cf. also Examples 1 to 6).

After the deactivation of the reaction mixture according to variant A, unreacted monomer and/or the deactivated catalyst can be separated off.

The process can also be stopped without chemical deactivation of the catalyst. For this purpose, the active catalyst is separated off from the reaction mixture immediately after the desired conversion has been reached in order to prevent further reaction, possibly with by-product formation. (Variant B).

Simultaneously with or after removal of the catalyst, unreacted residual monomer can be separated off from the reaction mixture treated according to variant B.

In the process of the invention, it is possible to use all known separation techniques, e.g. distillation, extraction or crystallization/filtration, to separate unreacted monomers, the catalyst and/or other undesirable constituents from the reaction mixture. Preference is given to distillation, if appropriate in the specific form of thin film distillation. Of course, it is also possible to employ combinations of two or more of these techniques.

To stop the reaction according to variant B, preference is given to removing the catalyst by distillation, with unreacted monomer being removed at the same time if appropriate.

In the work-up of the reaction mixture obtained after the reaction has been stopped according to variant A or B, the residual monomer present is preferably removed by distillation.

If the polyisocyanate prepared according to the invention is still to contain free, unreacted monomer, as is of interest for, for example, further processing to produce NCO-blocked products or polyuretdione hardeners which are low in or free of NCO, e.g. for powder coatings, the removal of monomer can be omitted after the reaction has been stopped (variants A and B).

In carrying out the process of the invention, it is immaterial whether the process is carried out fully or partly discontinuously or continuously.

Furthermore, additives and stabilizers customary in polyisocyanate chemistry can be added at any desired point in time in the process of the invention. Examples are antioxidants such as sterically hindered phenols (2,6-di-tert-butylphenol, 4-methyl-2,6-di-tert-butylphenol), light stabilizers such as HALS amines, triazoles, etc., weak acids or catalysts for the NCO—OH reaction, e.g. dibutyltin dilaurate (DBTL).

Furthermore, it can be useful to add small amounts of a catalyst poison to be used in variant A to a product which has been worked up according to variant B in order to increase the redissociation stability and to suppress the tendency to by-product formation, discoloration or further reaction of the free NCO groups with one another, e.g. during product storage.

Products prepared by the process of the invention which are based on optionally branched, linear-aliphatic diisocyanates or polyisocyanates and have no cycloalkyl-substituents are light in colour and have a viscosity of <1000 mPas/23° C. If cycloaliphatic and/or aralilphatic diisocyanates or polyisocyanates are used, highly viscous to solid resins are obtained (viscosity >10000 mPas/23° C.).

In low-monomer form, i.e. after unreacted monomer has been separated off, the products according to the invention have an NCO content of <30% by weight, preferably <25% by weight.

The polyisocyanates prepared by the process of the invention serve as starting materials for producing, for example, shaped bodies (if appropriate foamed), paints and varnishes, coating compositions, adhesives or additives, with the free NCO groups present which have not been converted into uretdione also being able to be blocked if appropriate.

To block the free NCO groups which have not been converted into uretdione, it is possible to use all methods known to those skilled in the art. Suitable blocking agents are, in particular, phenols (e.g. phenol, nonylphenol, cresol), oximes (e.g. butanone oxime, cyclohexanone oxime), lactams (e.g. ε-caprolactam), secondary amines (e.g. diisopropylamine), pyrazoles (e.g. dimethylpyrazole, imidazoles, triazoles) or esters of malonic and acetic acid.

The largely by-product-free polyisocyanates having uretdione groups which have been prepared by the process of the invention can be used, in particular, for producing one- and two-component polyurethane coating compositions, if appropriate in admixture with other diisocyanates or polyisocyanates of the prior art, e.g. diisocyanates or polyisocyanates containing biuret, urethane, allophanate, isocyanurate and iminooxadiazinedione groups.

Particular preference is likewise given to using the polyisocyanates which have been prepared according to the invention on the basis of optionally branched, linear-aliphatic isocyanates as reactive diluents for reducing the viscosity of highly viscous polyisocyanate resins.

To convert the polyisocyanates prepared according to the invention into polyurethane, it is possible to use all compounds which have at least two isocyanate-reactive functions, either individually or in any mixtures with one another (isocyanate reactive binder).

Preference is given to using one or more isocyanate-reactive binders which are known per se in polyurethane chemistry, e.g. polyhydroxy compounds or polyamines. As polyhydroxy compounds, particular preference is given to using polyester polyols, polyether polyols, polyacrylate polyols and/or polycarboxylic acid polyols, if appropriate with addition of low molecular weight, polyhydric alcohols.

The equivalence ratio of isocyanate groups which have not been converted into uretdione groups and may, if appropriate, also be blocked to isocyanate-reactive functions of the isocyanate-reactive binder, e.g. OH, NH or COOH, is from 0.8 to 3, preferably from 0.8 to 2.

It is possible to use an excess of isocyanate-reactive binder since the cleavage of the uretdione ring, if appropriate at elevated temperature and/or with addition of catalyst, leads to the setting-free of further NCO groups which can react with the excess of isocyanate-reactive functions. This increases the network density of the polymer formed and its properties are influenced in an advantageous manner.

To accelerate the crosslinking reaction of the polyisocyanates prepared according to the invention with the isocyanate-reactive binder, it is possible to use all catalysts known from polyurethane chemistry. For example, it is possible to use metal salts such as dibutyltin(IV)dilaurate, tin(II)bis(2-ethylhexanoate), bismuth(III)tris(2-ethylhexanoate), zinc(II)bis(2-ethylhexanoate) or zinc chloride and also tertiary amines such as 1,4-diazabicyclo[2.2.2]octane, triethylamine or benzyldimethylamine.

In carrying out the formulation, the optionally blocked polyisocyanate prepared according to the invention, the isocyanate-reactive binder, catalyst(s) and, if appropriate, the customary additions such as pigments, fillers, additives, levelling agents, antifoams and/or matting agents are mixed with one another and homogenized in a customary mixing apparatus, e.g. a sand mill, if appropriate using solvents.

Suitable solvents are all customary surface coating solvents known per se, e.g. ethyl and butyl acetate, ethylene or propylene glycol monomethyl, monoethyl or monopropyl ether acetate, 2-butanone, 4-methyl-2-pentanone, cyclohexanone, toluene, xylene, solvent naphtha, N-methylpyrrolidone, etc.

The coating compositions can be applied in solution or from the melt or, if appropriate, in solid form (powder coatings) to the article to be coated by customary methods such as painting, rolling, casting, spraying, dipping, fluidized-bed sintering or by electrostatic spraying processes.

Suitable substrates are all known materials, in particular metals, wood, plastics and ceramic.

EXAMPLES

The percentage figures for the conversion are calculated by dividing the amount of product obtained (polyisocyanate resin) by the total amount of starting materials used (diisocyanate monomer and catalyst) and multiplying by 100. All further percentages are, unless indicated otherwise, percentages by weight.

The dynamic viscosities were determined at 23° C. using a VT 550 viscometer from Haake, Karlsruhe. It was ensured that the flow behaviour of the described polyisocyanates which had been prepared according to the invention and also that of the comparative products corresponds to that of ideal Newtonian liquids by measurements at different shear rates. Indication of the shear rate can therefore be omitted.

The reported "mol %" and "molar ratio of various structure types to one another" are based on NMR-spectroscopic measurements. They are always based, unless indicated otherwise, on the sum of the structure types formed by the modification reaction (oligomerization) from the previously free NCO groups of the isocyanate to be modified.

$^{13}$C-NMR measurements were carried out on DPX 400, AVC 400 and DRX 700 instruments from Bruker, Karlsruhe, Germany, using about 50% strength samples in dry CDCl$_3$ or about 80% strength samples in D$_6$-DMSO ($^{13}$C-NMR: 100 or 176 MHz, relaxation delay: 4 sec, at least 2000 scans). As reference for the ppm scale, small amounts of tetramethylsilane in the corresponding solvent ($\delta$=0 ppm) or the solvent alone ($\delta$=77.0 ppm (CDCl$_3$) or $\delta$=43.5 ppm (D$_6$-DMSO)) were chosen.

Unless indicated otherwise, the reactions were carried out using freshly degassed HDI as starting material. The term "freshly degassed" means that the HDI used was freed of dissolved gases by stirring under reduced pressure (<1 mbar) for at least 30 minutes and subsequently blanketing with nitrogen immediately before the catalytic reaction.

All reactions were carried out under an atmosphere of dry nitrogen.

tert-Butyl-substituted phosphines were prepared from the corresponding chlorophosphines and alkylating agents such as alkyllithium or alkylmagnesium halides (Grignard compounds) by methods known from the literature (K. Sasse in Methoden der organ. Chemie (Houben-Weyl) 4th edition, Vol. XII/1, Georg Thieme Verlag, Stuttgart, 1963), as described below for an example.

Preparation of a Catalyst (not According to the Invention)

tert.-Butyl-di-n-butylphosphine ($^t$BuP"Bu$_2$)

10.3 g (65 mmol) of tert-butyldichlorophosphine (from Aldrich, 82018 Taufkirchen, Germany) were introduced under nitrogen in a 100 ml round-bottom flask at room temperature, dissolved in 20 ml of diethyl ether and cooled while stirring to −20° C. 55 ml of a 2.5 M solution of n-butyllithium in n-hexane (from Aldrich) were subsequently added dropwise, resulting in a white solid precipitating immediately with considerable evolution of heat. After the addition was complete, the mixture was warmed slowly to room temperature, subsequently refluxed for one hour, cooled to room temperature and admixed with 10 ml of 10% strength, oxygen-free, aqueous HCl, resulting in two clear, colourless phases being formed. After phase separation, the organic phase was freed of the major part of the solvent by distillation under atmospheric pressure, subsequently filtered and the filtrate was distilled under reduced pressure. This gave 7.4 g (56% of theory) of $^t$BuP"Bu$_2$, b.p.: 75° C. at 0.2 mbar.

di-1-Adamantyl-n-butylphosphine was procured from Strem, 77672 Kehl, Germany; 1-adamantyldi-n-butylphosphine was prepared from adamantylmagnesium bromide (J. Org. Chem. 47 1982 4120-4128) and chlorodi-n-butylphosphine (from Aldrich, 82018 Taufkirchen, Germany).

Examples 1 to 5

According to the Invention 10 g of freshly degassed HDI were in each case stirred under nitrogen in the presence of the amounts indicated in Tables 1 to 5 of the catalyst indicated there at the temperatures indicated by means of a magnetic stirrer bar in glass vessels closed by means of septa, with the progress of the reaction being checked at regular intervals by measuring the index of refraction (at 20° C. and the frequency of the light of the D line of the sodium spectrum, $n_D^{20}$) of the reaction mixture. The index of refraction measured immediately after homogenization of catalyst and HDI served as reference for the starting point of the reaction (conversion=0; $n_D^{20}{}_{start}$).

The parameters conversion (yield) and $n_D^{20}$ of the reaction mixture have a virtually linear relationship according to the following formula:

Conversion [%]=19.85*$n_D^{20}$−28.74

(cf. DE-A 103 54 544), in the yield range up to about 60% of uretdione-polyisocyanate resin in the reaction mixture.

The $n_D^{20}$ is the value of the index of refraction which has been obtained using the abovementioned reference value for the "HDI- and HDI oligomer content" according to the following formula:

$n_D^{20}$=measured value−($n_D^{20}{}_{start}$−$n_D^{20}{}_{HDI}$).

The values for the conversion given in Tables 1-5 have been determined from the measured indices of refraction on the basis of the abovementioned relationships.

To determine the selectivity, the conversion samples were admixed with the amount of elemental sulphur corresponding to their phosphine content in order to suppress further reaction and examined by NMR spectroscopy. To allow a better overview of the selectivities, the parameter U/T was defined as the molar ratio of the uretdione structures to the sum of the two trimer structures (isocyanurate and iminooxadiazinedione).

TABLE 1

Catalyst: $^t$BuP"Bu$_2$ (1.5 mol %, based on HDI)
Reaction temperature: 30° C.

| HDI conversion [%] | U/T |
|---|---|
| 11% | 12 |
| 21% | 10 |
| 31% | 9 |
| 40% | 8 |
| 56% | 7 |
| 62% | 6 |

TABLE 2

Catalyst: $^t$BuP"Bu$_2$ (0.6 mol %, based on HDI)
Reaction temperature: 80° C.

| HDI conversion [%] | U/T |
|---|---|
| 8% | 27 |
| 17% | 17 |
| 35% | 8 |
| 41% | 6 |

TABLE 3

Catalyst: $^t$Bu$_2$P"Bu (3.7 mol %, based on HDI)
Reaction temperature: 80° C.

| HDI conversion [%] | U/T |
|---|---|
| 8% | 68 |
| 14% | 48 |
| 18% | 13 |
| 31% | 6 |
| 41% | 5 |

TABLE 4

Catalyst: 1-Adamantyldi-n-butylphosphine (1.4 mol %, based on HDI)
Reaction temperature: 80° C.

| HDI conversion [%] | U/T |
|---|---|
| 10% | 17 |
| 20% | 13 |
| 45% | 5 |
| 52% | 4 |

TABLE 5

Catalyst: di-1-adamantyl-n-butylphosphine (2.3 mol %, based on HDI)
Reaction temperature: 80° C.

| HDI conversion [%] | U/T |
|---|---|
| 6% | 48 |
| 20% | 14 |
| 30% | 9 |

Examples 6 and 7

Comparative Examples 10 g of freshly degassed HDI were in each case stirred under nitrogen in the presence of the amounts indicated in Tables 6 and 7 of the catalyst indicated there at the temperatures indicated by means of a magnetic stirrer bar in glass vessels closed by means of septa, with the progress of the reaction being checked at regular intervals as described above. As can be seen from the values in Tables 6 and 7, the catalysts according to the invention have significant advantages in terms of uretdione selectivity at a given HDI conversion over their closest counterparts having monocycloalkyl or bicycloalkyl substituents on the phosphorus (with a secondary carbon atom bound to P).

TABLE 6

Catalyst: Cyclohexyl-P-$^n$Hex$_2$ (0.5 mol %, based on HDI)
Reaction temperature: 80° C., cf. DE 102 54 878, Example 1

| HDI conversion [%] | U/T |
|---|---|
| 15 | 7 |
| 35 | 4 |
| 45 | 3 |
| 60 | 2 |

TABLE 7

Catalyst: 2-Norbornyl-P-$^n$Hex$_2$ (0.3 mol %, based on HDI)
Reaction temperature: 80° C., cf. DE 103 54 544, Example 3

| HDI conversion [%] | U/T |
|---|---|
| 12 | 19 |
| 16 | 15 |
| 20 | 13 |
| 33 | 6 |
| 37 | 5 |
| 40 | 4 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the dimerization of isocyanates, in which
   a) at least one organic isocyanate,
   b) a catalyst containing at least one phosphine which has one or two tertiary alkyl radicals bound directly to phosphorus,
   c) optionally solvents and
   d) optionally additives are reacted.

2. The process according to claim 1, wherein the phosphines correspond to the formula I:

formula I where
   $R^1$ is an optionally singly or multiply $C_1$-$C_{12}$-alkyl- or $C_1$-$C_{12}$-alkoxy-substituted, tertiary alkyl radical whose tertiary carbon atom is bound to the phosphorus atom via a covalent (single) bond,
   $R^2$ is a radical from the group consisting of primary and secondary, singly or multiply $C_1$-$C_{12}$-alkyl- or $C_1$-$C_{12}$-alkoxy-substituted, optionally branched, optionally cycloaliphatic $C_1$-$C_{20}$ radicals, with the proviso that the carbon atom bound to the P atom bears at least one hydrogen atom, and
   $R^3$ corresponds to $R^1$ or $R^2$.

3. The process according to claim 2, wherein $R^1$ in formula I is tert-butyl, tert-amyl or adamantyl.

4. The process according to claim 1, wherein aliphatic, cycloaliphatic or araliphatic diisocyanates or polyisocyanates having an NCO functionality of ≧2 are used for component a).

5. The process according to claim 1, wherein the dimerization is carried out at a temperature of from 0 to 150° C. to a conversion of the NCO groups of from 5 to 90 mol % and is then stopped.

* * * * *